United States Patent [19]

Desjacques

[11] 4,367,527

[45] Jan. 4, 1983

[54] POCKET CALCULATOR FOR THE FORECASTING OF TEMPORAL CYCLES

[75] Inventor: Edmond Desjacques, Thônex, Switzerland

[73] Assignee: Bioself International Inc., Nassau, The Bahamas

[21] Appl. No.: 196,048

[22] PCT Filed: Aug. 9, 1979

[86] PCT No.: PCT/CH79/00108

§ 371 Date: Apr. 9, 1980

§ 102(e) Date: Mar. 17, 1980

[87] PCT Pub. No.: WO80/00384

PCT Pub. Date: Mar. 6, 1980

[30] Foreign Application Priority Data

Aug. 7, 1979 [CH] Switzerland .................. 8455/78

[51] Int. Cl.³ .................. A61B 5/00; G06F 15/02
[52] U.S. Cl. .................. 364/413; 364/415; 364/705; 364/715; 365/166; 128/738
[58] Field of Search ............ 364/413, 415, 557, 705, 364/715, 900; 365/166; 128/736, 738; 368/34; 235/92 T

[56] References Cited

U.S. PATENT DOCUMENTS

| | | | |
|---|---|---|---|
| 3,042,900 | 7/1962 | Werts | 365/166 |
| 3,134,908 | 5/1964 | Ellwood | 365/166 |
| 3,813,533 | 5/1974 | Cone et al. | 364/705 |
| 3,973,110 | 8/1976 | Rode et al. | 364/715 |
| 4,054,948 | 10/1977 | Grier et al. | 364/900 |
| 4,059,952 | 11/1977 | Kaestner | 368/34 |
| 4,084,249 | 4/1978 | Schlick | 364/705 |
| 4,101,962 | 7/1978 | Hakata | 364/413 |
| 4,151,831 | 5/1979 | Lester | 364/415 |
| 4,168,525 | 9/1979 | Russell | 235/92 T |

Primary Examiner—Errol A. Krass
Assistant Examiner—Gary Chin
Attorney, Agent, or Firm—Trexler, Bushnell & Wolters, Ltd.

[57] ABSTRACT

The memory (80) is intended to be read or modified by an electronic logical system of a pocket calculator. It comprises a plurality of bistable electromechanical flip-flop circuits (82). Each flip-flop circuit (82) comprises an input for setting at 1 (S) and an input for setting a zero (R) and an output (78). The inputs are connected individually to a multiplexor (702) controlled by a control circuit (701). The control circuit (701) is connected in two directions with a central processor via a bus (51). The control circuit (701) manages readings and writings to the memory (80).

The memory is intended to memorize data which have to be retained in the calculator in a reliable and convenient way, even if the supply is cut off. The calculator is, for example, intended to make calculations concerning the application of the Ogino method, the data to be memorized being the durations of previous cycles and the date of the last period.

13 Claims, 13 Drawing Figures

POCKET CALCULATOR FOR THE FORECASTING OF TEMPORAL CYCLES

We know how to realise miniature calculations capable of effecting relatively complex calculations.

Moreover, there are known methods allowing a woman to forecast, with a given margin, the times when sexual intercourse will probably be followed by a pregnancy. The Ogino method is such a method. The realisation of a miniature calculator specially for forecasting times according to one method or another presents no problem in principle. However, a serious problem is posed over the retention of basic data. Standard calculators, in fact, are designed in such a way that the user must supply data at the moment when he wishes to solve a problem, and must specify the nature of the calculations, the machine only having in its memory sequences of instructions corresponding to basic operations and some basic constants. The calculator is not usually designed to retain data. Now, if one wishes to make a forecast, it is essential to have at one's disposal dates of some previous periods. To make a forecast with a reasonable safety margin, account will be taken, for example, of an average relating to the last four periods.

These data are significant and they must be retained from month to month. For these data, a conventional memory circuit which is cleared when the supply is cut off evidently cannot be used.

In certain calculators, used is made of miniature magnetic cards. However, such a means does not here constitute absolute safety. In fact, the magnetic card may be mislaid and the data it contains may be erased or altered by the influence of a magnetic field coming into contact with the card.

The present invention refers to the supplying of a convenient and reliable solution to the problem of retaining some essential data, especially in the instance of a pocket calculator used for the forecasting of menstrual cycles.

The calculator according to the invention forms the object of claim 1, the other claims relating to special forms of execution.

The calculator according to the invention offers a convenient solution for those wishing to use a method of forecasting such as the Ogino method. The essential data are memorized in a special memory incorporated in the calculator and not in an external storage medium of the magnetic card type. Consequently there is no risk of mislaying it.

Furthermore, the memory thus incorporated in the calculator runs practically no risk of being directly in contact with a magnet which could disturb it, and the memory is thus far more reliable than a memory on magnetic card.

Finally, if a suitable type of electromechanical element is chosen, the electromechanical memory will show a good immunity to exterior influences such as impacts and variations in temperature and pressure. In particular, a preferrred type of electromechanical element is protected against an acceleration on the order of 10 g.

The calculator can be realised in such a way that its use is simplicity itself and requires from the user only a minimum of commonsense and care. Conversly, it can be connected to a relatively complex calculator and/or to a digital clock.

Sometimes, for psychological reasons, the person will need a forecasting programme different from a standard programme and according to the directions of a gynaecologist, for example. To this end, provision can be made for a particular embodiment in which the memory carrying the programme comprises a removable or reprogrammable part. For example, the memory unit of the calculator can consist of a ROM memory comprising the standard forecasting programme and replaceable by a different memory, programmed on the basis of the directions of the gynaecologist; or else, the memory unit comprises an EPROM memory, that is to say, erasable, in principle, by means of intense ultraviolet rays, and reprogrammable by means of an auxiliary apparatus which could be in the possession of the gynaecologist or the company distributing the calculator.

A calculator according to the invention can consequently be advantageously applied to the forecasting of the woman's menstrual cycles, especially according to the Ogino method; nevertheless, the basic principles of the invention can be applied to any problem which can be put through a miniature calculator and of the kind in which one wishes to retain, from one period of time to another, a certain number of essential data which requires a reliable memory, incorporated in the calculator and retaining data independently of the electrical supply.

The calculator according to the invention could be advantageously adapted to the calculation of biorhythms. A biorhythm calculator with essentially electronic working is known. However, this known calculator presents the drawback of a volatile memory, that is to say, in which the data are lost when the supply is cut off. The calculator according to the invention will, in such an instance, allow this drawback to be corrected, and, even if the supply is cut off, will allow the retention in the memory (this being an electrical reading and writing memory) of a calculation datum such as the date of birth, so that it will be usable when the supply is restored.

A biorhythm calculator in which the writing of curves is effected by means of electromechanical parts is known from the Swiss Pat. No. 578 766. If the supply is cut off, the cogwheels maintain their position so that the writing of the curves could be achieved after restoration of the supply. But this obviously does not constitute a true memory which can be reread by a calculation circuit and nothing is provided to memorize a datum such as the date of birth in an electromechanical memory retaining the datum even if the supply is cut off, for example between two usings. The calculator described in this patent consequently cannot be compared to the present invention.

The present invention could also be advantageously adapted to a digital alarm for retaining the hour for the activating of the striking mechanism, even in the event of the supply being cut off.

In that way, dates could also be memorized in the instance of the alarm clock including an electronic calendar and means for signalling the imminence or the occurence of the date which the user has written to the memory of the alarm. This signalling means can, for example, be a flickering of one part of the display. The solution according to the invention would, for example, allow the changing of batteries without fear of losing or altering the important date or the noted hour.

What precedes shows the advantage of the present invention in the field of electronic miniature apparatuses which are not pure calculators but which, nevertheless, as in the case, for example, of a digital alarm, comprises one or several functions using data, for example the alarm hour, which it is desirable to retain in a convenient and reliable way, even if the supply is cut off.

The invention concerns also the field of mini electronic devices which are not pure calculators but which, however, as for example a digital alarm clock, comprise one or several functions utilising data, for example the time of alarm, data it is desirable to preserve in a convenient and reliable manner, even if the supply is cut.

The invention will be better understood by means of the description of a few embodiments given hereafter by way of example and by reference to the drawings.

FIG. 1 represents an embodiment of the calculator according to the invention,

FIG. 2 represents in a diagrammatic way the circuits of the calculator of FIG. 1, FIG. 3 represents the plan of a memory with electromechanical elements, FIG. 4 represents an electromechanical memory element, FIG. 5 illustrates another embodiment of the calculator, FIG. 6 illustrates a third form of the execution of the calculator, FIGS. 7A, B and C illustrate the states of a special display element, FIGS. 8A, B and C illustrate various contents of the display, and FIG. 9 represents in a diagrammatic way the circuits of the calculator in FIG. 6.

The calculator represented in FIG. 1 comprises a unit 1 containing the circuits and on which are disposed the control and reading units.

The control parts consist of a keyboard 2 comprising an ON/OFF key 22 for starting and stopping, numerical keys such as the key 24, function keys 25 for indicating the nature of the datum supplied, day, month, year, an instruction key 26 for requesting a forecast, and a writing key 29, provided with a safety key 28 such that writing can only be done if the keys 28 and 29 are simultaneously pressed.

The calculator also comprises a display including electroluminescent diodes, green 31, yellow 32 and red 33. These diodes are intended to indicate the probability that a possible act of sexual intercourse may be followed by a pregnancy according to the following convention: red light, high probability; yellow light, average probability; green light, low probability.

The display also includes a digital part comprising at least six cells 42 with seven segments, either of the electroluminescent type or with liquid crystals, to display numerically the day, month and year (units and tens of the number of the Civil year). The inscriptions 40 such as "DAY", "MONTH", "YEAR" facilitate reading of the date.

The necessary logical functions are realisable in principle by means of circuits such as gates, registers, counters, etc. However, in practice, one will start with more developed circuits of the microprocessor type, more flexible in use and more convenient to implement when the functions to be realised go beyond the level of elementary functions such as simple counting or conditional transfer.

The plan of FIG. 2 comprises a miniature logical system organised around a central processor unit CPU 50, controlling memories and peripherals through the intermediary of a bus 52. As peripheral, the keyboard 2 is to be found connected by lines 55 to an interface circuit 54 connected to the processor CPU 50 by the bus 52. As peripheral, the display 3 is also found connected by lines 57 to an interface circuit 56 connected to the bus 52.

The programme intended to be carried out by the processor is housed in a ROM memory 60, that is to say a ROM memory which, by means of auxiliary apparatuses, can be programmed at will. This memory is preferably implemented in the form of a removable "chip", that is to say, a miniature circuit provided with pins intended to be connected in a base provided with corresponding connectors. A removable chip can be taken out to be modified or replaced. An EPROM can be used, that is to say a circuit erasable, in principle, by means of intense ultraviolet rays, and reprogrammable by means of an auxiliary device ad hoc.

The calculations make use of auxiliary variables and of data from the keyboard which must be memorized in a RAM memory 62. However, if there is not too great a number of these variables, it can be worth bearing in mind that the processor includes the means required for memorizing them. Known processors usually comprises a plurality of registers intended for this purpose.

Thus the calculator aims at performing a certain number of functions for solving the problem set forth hereinabove. To do that one utilises a microprocessor controlling a certain number of peripherals, as explained above, by means of a program. Any person skilled in the field of microprocessors is able to realize this program put in the ROM 60 memory in "ASSEMBLER" language, according to the problem set. This person will use for example a microprocessor of "6500" type, ROM and RAM memories of "8 bits" type and interfaces type "6520", all manufactured for example by "Synertec" or "Intel", these manufacturers supplying also the corresponding user's manuals describing accurately the operation of these devices.

There also exist "chips" simultaneously incorporating a PROM memory, an EPROM memory part and the central processor CPU itself. The principle of the plan stays the same, but such a circuit can offer the advantage of a reduced bulkiness. One will refer preferably to type TMS of TEXAS INSTRUMENTS.

In the plan of FIG. 2, one again finds a memory 80 with electromechanical elements connected to an interface circuit 70 by lines 72 and 90. Such a memory presents particular details connected with the principles underlying the present invention. This memory is also controlled by the microprocessor programmed to this effect.

FIG. 3 shows the plan of the electromechanical memory 80 and of its interface 70.

The memory is composed of a plurality of electromechanical memory elements 82. Each element 82 can be compared to a flip-flop circuit, being consequently able to memorize an information of 1 bit, and the element will be described in more detail in FIG. 4.

Each flip-flop circuit comprises an input S (set) for setting at 1 and an input R (reset) for setting at zero, and an output wire 78, all the output wires being connected in one single output wire 90 for the whole memory 80.

The inputs R and S of each element 82 are individually connected to one of the outputs of a multiplexor 702. The choice of the output is controlled by the control wire 73 of the multiplexor and the wire 74 is used to determine if an R or an S is required. When the mulitplexor has selected the appropriate output as a function of the address (wire 73) and of the datum (wire 74), a command instruction can be sent by the wire 75 and it will be switched by the multiplexor towards the selected input.

The writing pulse R or S must have a certain power and a certain duration, for example 10 milliamperes for 2 milliseconds, to excite the electromechanical parts of the element 82.

To read, a pulse is also sent by the multiplexor to the input S of the element 82 which one wishes to read, but a much shorter pulse is sent, for example 10 microseconds. This pulse cannot alter the logical state of the flip-flop circuit. At this moment, if the flip-flop circuit is at 1, the output 78 and the datum wire 90 will supply a logical 1, and if the flip-flop circuit is at zero, the output 78 and the datum wire 90 will remain at 0, so that, for 10 microseconds, one has at one's disposal the logical value of the flip-flop circuit chosen on the datum wire 90, which is sufficient for the reading.

The multiplexor 702 is itself controlled by the microprocessor through an amplifier 701, the microprocessor managing the writings and the readings in the memory 80. The amplifier 701 is obviously in communication in both directions through a bus 52 with the processor 51 on which it depends. It may be formed simply of a transistor amplifier. The control circuit 701 and the multiplexor 702 can be considered as forming the interface of the memory 80.

FIG. 4 represents the plan of the electromechanical memory element 82. The element comprises a bistable contact 85 comprising a strip 89 connected to a terminal 86 and establishing contact either with the terminal 88, as in the figure, or with the opposite terminal 87. Switching is controlled by two windings 83 and 84. A pulse on the winding 83 makes the strip 89 come into position represented in FIG. 4 and a pulse on the other winding 84 makes the strip come into the opposite position, indicated in dotted line. One winding is connected to the input S and the other winding is connected to the input R. Furthermore, the input S is connected to the terminal 88, to allow readings.

The matrix of the memories 80 represented in FIG. 3 is realisable in the form of a printed circuit plate carrying a plurality of miniature bistable relays 82 welded to the plate by their contact terminals. A suitable relay model is the relay of the TL series supplied by the Deutsch Company. Such a relay withstands such conditions as a vibration of 3000 Hz exhibiting an acceleration of 30 g or an acceleration of 100 g for 6 milliseconds. Its bulkiness is of the order of a cubic centimeter or less so that several tens can be easily be housed in the unit of a calculator while remaining within the dimensions acceptable for a pocket calculator. Such relays are found on the market. One will use preferably relays of the series "TL" of the Deutsch Company.

Before proceeding with the description, it is essential to recall roughly what the known method for forecasting consists in.

The person notes the dates of her successive periods. The duration is calculated, in number of days, between two consecutive dates. When this duration is regular to within some days for several successive cycles and when this duration is between about 21 and 37 days, the method which proceeds from the principle that ovulation takes place 13 days before the beginning of the period can be justifiably applied. The probability that an act of sexual intercourse will be followed by a pregnancy is maximal, then, at the moment of ovulation. This probability is also raised for the four preceding days and the three days following.

This probability subsequently becomes almost zero approaching the next period. The rest of the time, there remains a relatively low probability of pregnancy.

An example of the method consequently consists in noting the dates of successive periods $d_1$, $d_2$, $d_3$ . . . , in calculating the corresponding durations of the cycles $C_1$, $C_2$, $C_3$ . . . , in verifying that they are regular, in establishing the average cm and the probable error ec. The probable date dp of the next period is calculated. This date is, of course, equal to the date of the last periods dn, plus the average duration of the cycle cm, with an uncertainty em:

$$dp = dn + cm \pm em$$

The number of days there are between today's date, da, and the probable date, dp, is calculated. If g is this number of days: $g = dp - da$. If g is between $14 + 4 + ec$ and $14 - 3 - ec$, then the probability of a subsequent pregnancy is high. If g is greater that $14 + ec + 4$, the probability is average. If g is less than $14 - ec - 4$, then the probability is low.

With regard to the calculator, one sees that the important data to be memorized are: the date of the beginning of the last period and the duration of the last four cycles in order to be able to establish an average. The memorizing of a date involves a memory part able to register a number j having an arbitrary value between 1 and 365, for the day in the year, as well as a number "a" between 0 and 99 for designating the year.

The date thus requires 9 bits for j and 7 bits for "a". As for the durations of cycles c, they are only considered valid if they are between 22 and 37 . Only the difference dc, then, between the duration of the cycle c and 22 is registered:

$$dc = c - 22$$

As c is equal at the most to 37, dc is equal at the most to 15 :

$$15 = 37 - 22$$

dc is consequently between 0 and 15 , which requires 4 bits. As 4 periods are registered, this requires $4 \times 4 = 16$ bits. The capacity of the memory 80 must consequently be at least 16 bits for the durations of cycles, plus 7 for "a", that is, 32 bits in all.

If five bits and not four are taken for each period, a band of values having double the extent can of course be covered, that is to say for a dc going from 0 to 31. In this case, one can calculate the difference dc from a lower limit which would be lower than 22 , and go to an upper limit higher than 37. The band of values for the durations c, for example, could be between 14 and 45. Of course, the programme will have to take account of the fact that the extreme values will not allow application of the method and will cause a signal indicating that to appear on the display.

Use and functioning are now going to be described with reference to FIGS. 1 and 2 in particular.

It is assumed that the memory 80 contains the date of the last period as well as the values (diminished by 22) of the durations of the last four cycles, that one finds oneself in conditions in which the method is applicable and that one is in May 1988.

The interested party wishes to obtain the forecast for the next day, which is the 20th of the month. To this end, she operates the keys on the keyboard carrying the symbols according to the following sequence:

J20M05A88* which means: day: 20, month: 5, year: 88, calculating instruction (key 26). The processor 50 commands the display of these numbers when the person writes on the keyboard. The processor 50 calculates the average duration cm of the cycle on the basis of the last four cycles, the probable error ec, the number g of cycles between this probable date and the date of the 20th, by, of course, consulting the memory 80, without altering it.

The processor calculates, according to g, cm and em, whether the probability is high, average or low and, according to the result, lights up one of the three diodes red 31, yellow 32 or green 33, respectively.

With regard to the calculation of time intervals between different dates, the calculator puts into operation means similar to those put into operation in some financial pocket calculators, which are supplied with what is called an electronic perpetual calendar. In the case of the calculator described here, the said means simply comprise an adequate programme and some fixed data, all written to a part of the ROM memory 60 which is used by the processor 50.

Of course the programme moreover preferably possesses routines allowing disclosure of instances when reasonable forecasting cannot be established, for example because the date for which forecasting is required is too far away or impossible, or because the cycles are too irregular or too short. The programme preferably then provides for the display of the letter E, for "error", followed, if need be, by a number indicating the nature of the error, allowing the person to refer to the instruction-book generally attached to the calculator or printed on the back of the calculator.

Of course it would be advisable to inform purchasers to avoid their making extreme demands on the calculator.

With regard to the modification of data, this occurs when the person writes the date of her last period. If it occurs, for example, on the May, 28th 1988, the person will operate the keys

J28 M05 A88, she checks on the display that the date is quite correct and then she simultaneously operates the registering key 29 and the safety key 28.

This sets in motion a programme for updating the date of the memory 80. This programme calculates the last cycle duration by the difference between the date of the preceding period still written in the memory 80, and the date of the recent period, which has just been supplied by means of the keyboard 2. It eliminates from the four cycle durations memorized those which concern the most distant cycle, shifts the other three and writes the duration of the most recent cycle. The programme replaces the date of the period again by the last date.

Of course, the memory 80 preferably comprises a greater number of elements than the required minimum, which is 32, as has been seen, in order to be able to write before clearing so that the data are not lost in the event of the supply being cut off during transfer. The memory will moreover include state bits to indicate whether the registering operation is complete or incomplete and to facilitate the recovery of data in the event of the supply being cut off during transfer.

Furthermore, for the four cycle durations, the memory can include a sensor which says which of the four is the most recent, it being understood that the others are arranged in a circular "stack". Two bits will be sufficient for the sensor.

The Ogino method can be completed by a test concerning temperature. The principle is adequately described in medical literature.

A variant of the calculator can then include a means for the introduction of the datum relating to the temperature and programmes for completing calculations with a function taking into account these data. A supplementary key will be sufficient for input means. Suppose T to be such a supplementary key.

The following could be its use: when the person requires a forecast, she writes on the keyboard not only the date but also the temperature, for example 37.3° C., before requesting the forecast by operating the key 26. The sequence would be:

J20M05A88 then, after checking on the display: T 3 7 3 and then * in order to command the calculation of a forecast.

As regards the writing of a date on the keyboard, it is quite clear that one could write the day, month and year in a different order. Furthermore, if one realizes that one of the instructions, for example the month, is wrong, all one has to do is operate the key M again and then the correct numerical keys.

Again, it can be noted that the key * 26 can be eliminated. In this case, the programme is arranged so as to make the forecast for any date written and which appears on the display. What precedes concerns an example of realisation and a number of modifications can be made without going beyond the scope of the present invention.

FIG. 5 illustrates a second embodiment which is characterized by a certain simplicity in the keyboard. The logical system of such a calculator essentially possesses the structure described in FIG. 2. However, the programmes take into consideration the keyboard peculiar to this form of execution.

Use and functioning are described hereafter at the same time as the functions of the different keys are described.

The key "1" 127 is used for bringing into service, connecting the supply. The key "0" 128 is used for stopping and cuts off the supply. However, even if the key "0" is not operated, the display is reduced to a minimum at the end of a minute if no key on the keyboard has been operated. The display is activated again if the key 1 is again pressed or if another key is also operated, excluding the key 0 which stops everything. If no key is operated for 5 minutes, the system is also halted.

The key J is used to modify a numerical counter whose contents are displayed on the two digits of the window 141. The said numerical counter is evidently essentially logical (soft); there is consequently no reason to describe it here.

If the number displayed is greater than the date of the day which the user wishes to display, the user can use the reversal key 125, which has the effect of reversing the counting direction.

The programme is so arranged that counting will be relatively slow when the key J is operated, and then at the end of some seconds, counting will accelerate if the key J is held down.

The key M 122 allows display of the month on the digits of the window 142 and the key A 123 allows display of the year on the two digits of the window 143. The keys M and A have functions similar to that of the key J and are also influenced by the reversal key 125.

The keyboard can include a key 126 ordering the calculation of a forecast. It has been seen that such a key is not indispensable. The keyboard finally includes keys for writing 28 and safety 29 whose function has already been described.

FIG. 6 illustrates an example of realisation which, conversely to that of FIG. 5, is characterised by a certain complexity. The keyboard comprises numerical keys and various function keys and could be perfectly suitable for a scientific, financial, arithmetical or other calculator, as well as an electronic clock. The keyboard furthermore includes a writing key 29 and a safety key 28.

The display 300 comprises, in the given example, an alphanumeric 301 area with three positions, a numerical area 302 with four positions and a special area 303 for the displaying of the forecasting calculation.

A low probability is displayed in the way indicated in FIG. 7A, an average probability is displayed in the way indicated in FIG. 7B, a high probability is displayed as indicated in FIG. 7C and, furthermore, by a flickering of the special display element 303. The display 300 can be advantageously but not exclusively realised according to the technique of liquid crystals.

FIG. 9 shows the plan of a calculator including a part used for the measurment of time. This part comprises a time base 174 connected to an assembly of logical circuits for time measurement 170 which functions permanently and, among other things, calculates not only the hour to within the second, but also the date. These circuits 170, 174 are intended to function without interruption.

Such a permanent time measurement circuit represents a convenient means for making the date of the day appear, as datum. This date can then be used for a forecasting calculation or a writing.

FIG. 8A illustrates the display of the hour, 10 hrs 25 in the morning in the given example. The alphanumeric area is used to distinguish the morning ("AM") from the afternoon ("PM").

FIG. 8B illustrates the display of a date, Nov. 12 th 1988 in the given example, as well as the display of a forecasting calculation which indicates, in the given example, an average probability.

Figure 1:
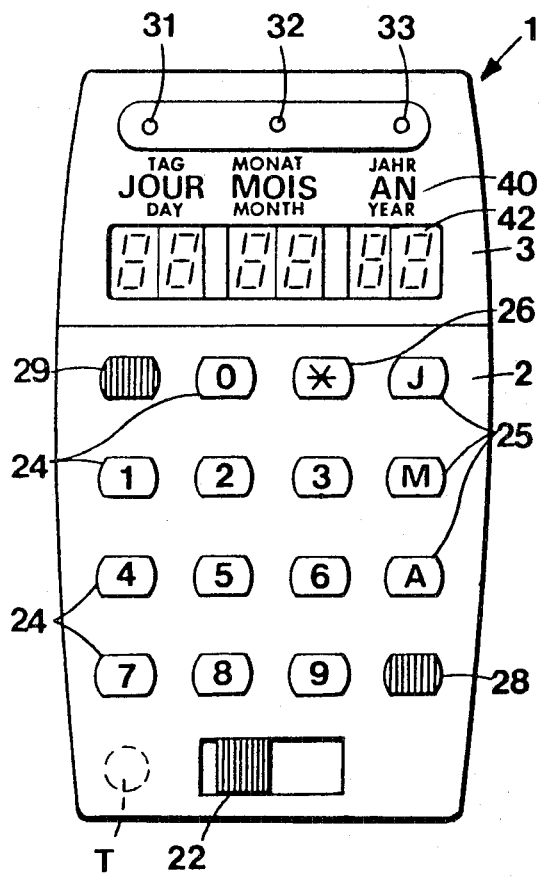
Figure 5:
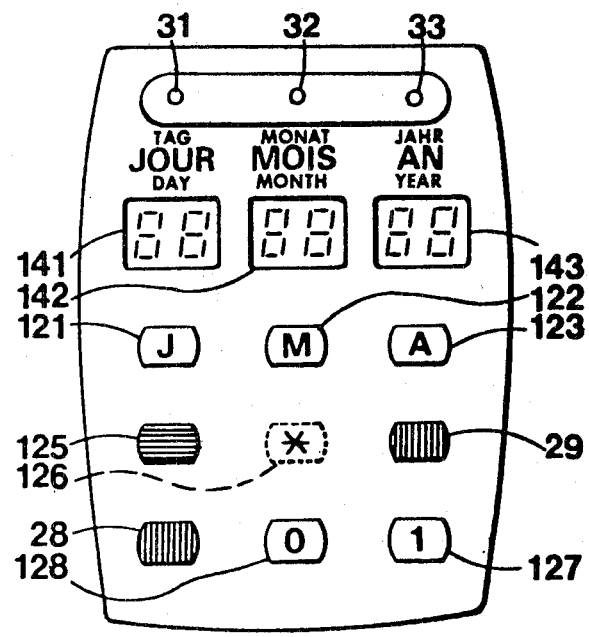
Figure 2:
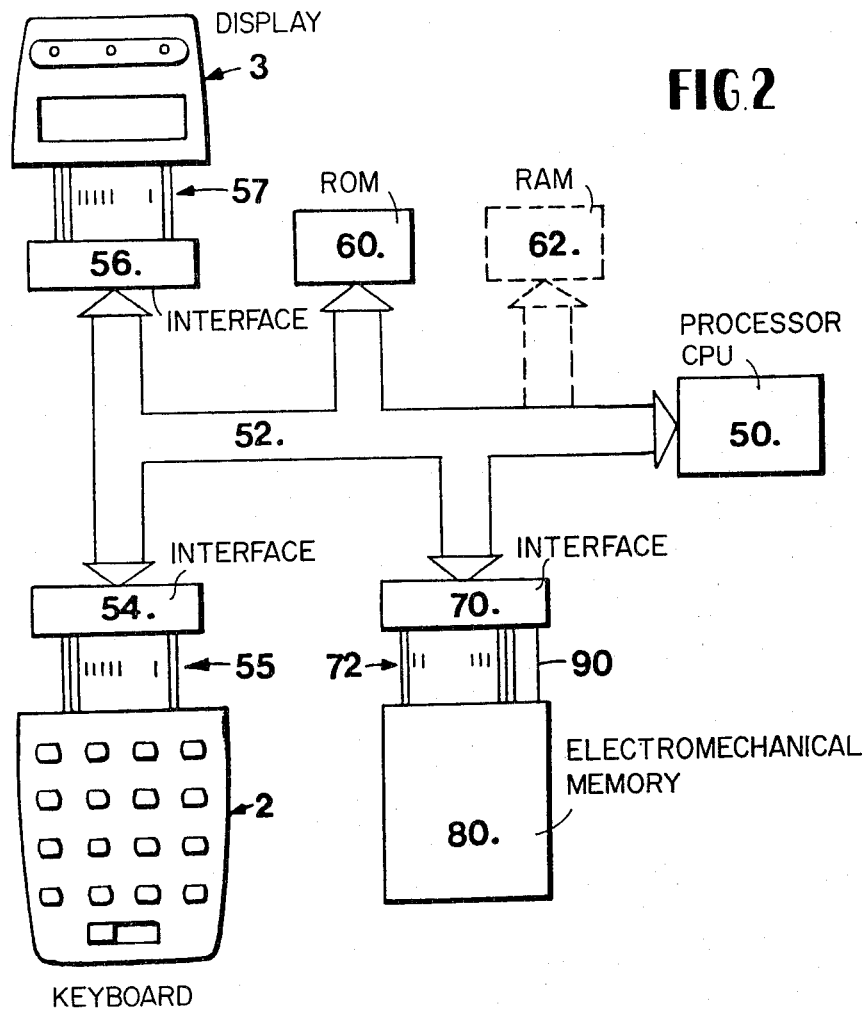
Figure 4:
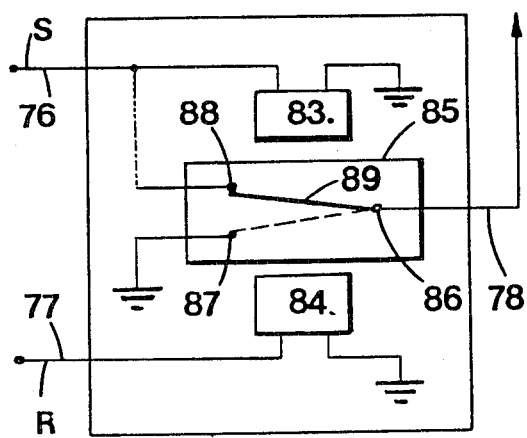
Figure 3:
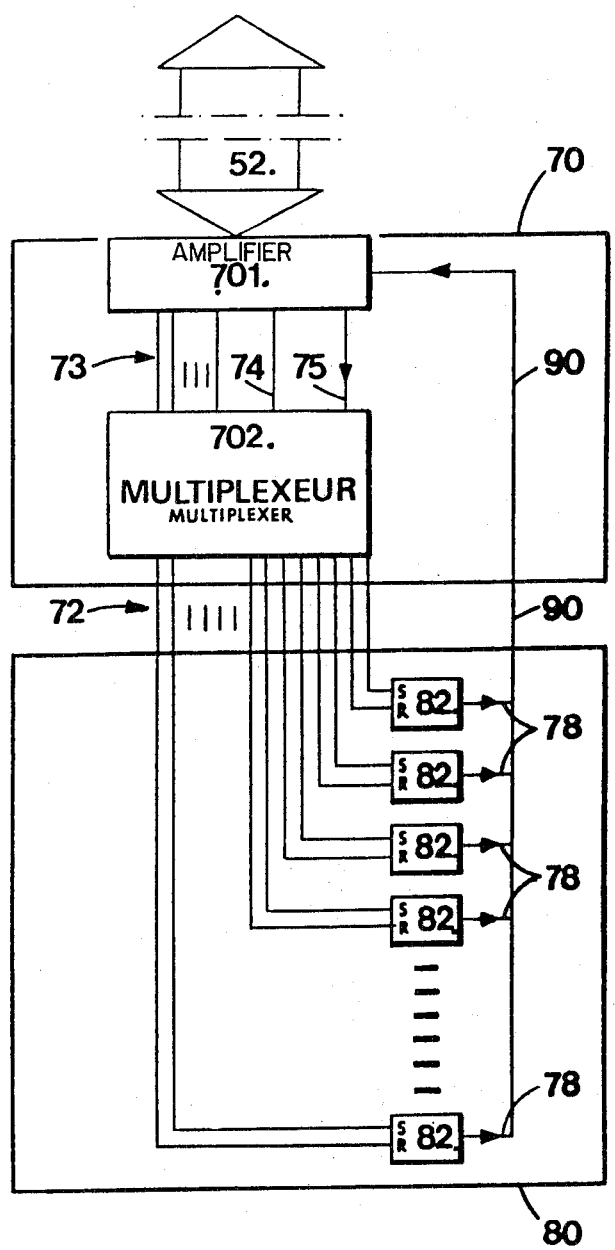
Figure 8:
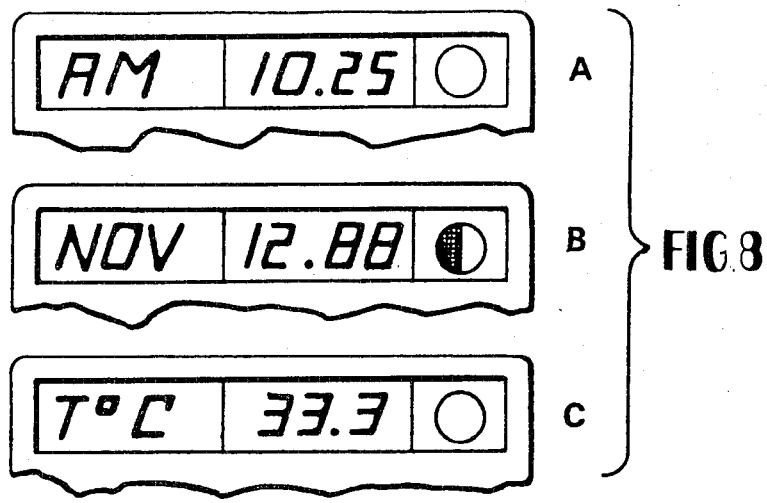
FIG. 8 illustrates some possible states of the display 300.
Figure 6:
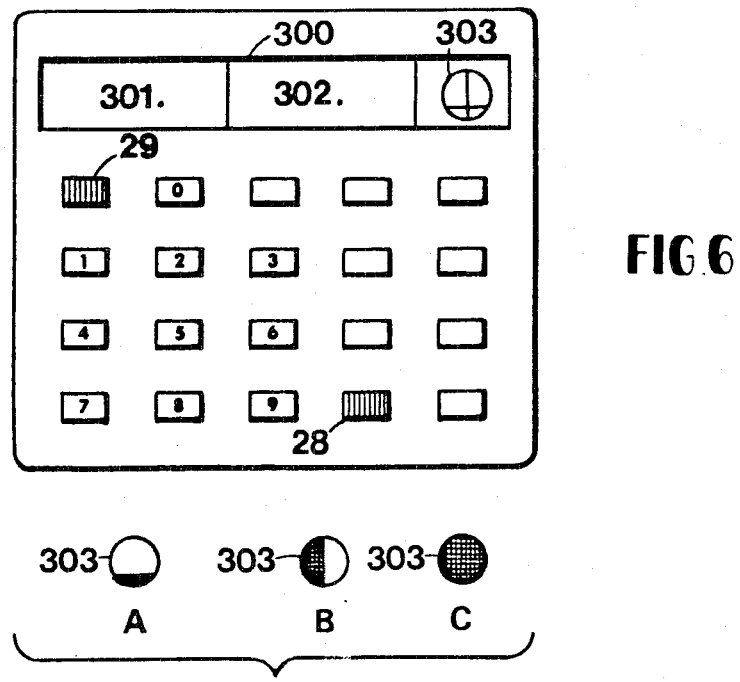
Figure 7:
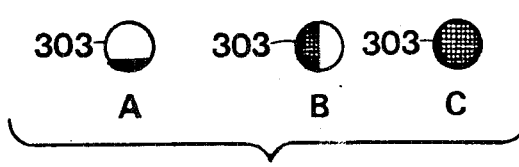
Figure 9:
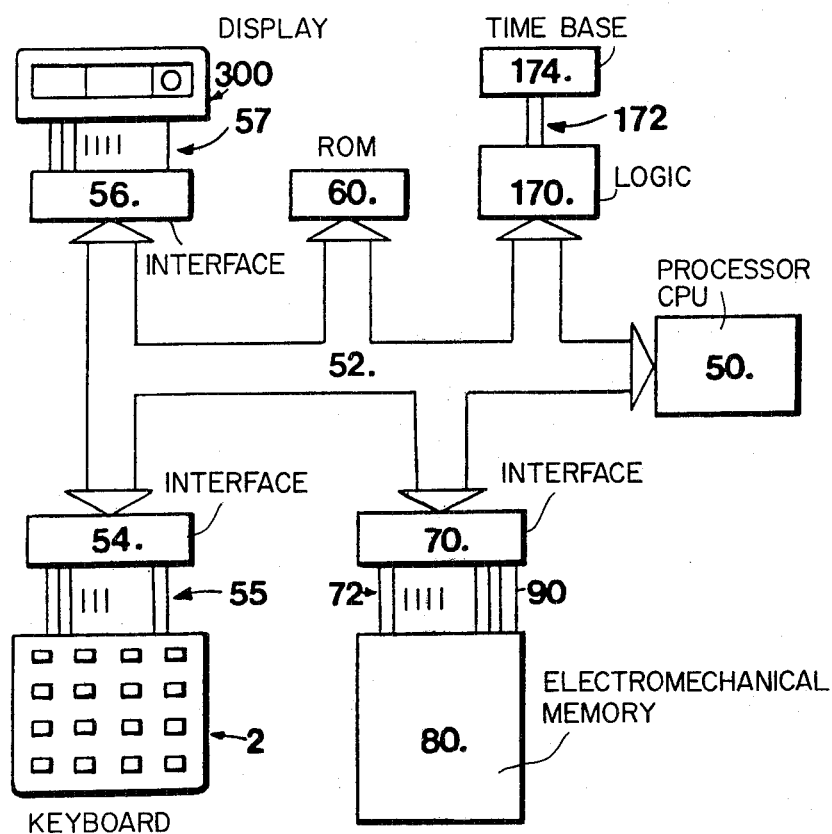

FIG. 8C indicates a third use of the display, provided for the instance in which one wishes to supply the forecasting calculation programme with a datum concerning the temperature, which is 37.3° C., in the given example.

The examples described above especially refer to a calculator specially arranged for carrying out calculations required by the Ogino method or a similar method. However, the principle consisting in using an electromechanical memory composed of a plurality of bistable relays and readings and registering circuits can be applied to other calculators or other electronic apparatuses including a digital part using data, when certain significant data must be memorized in a convenient and reliable way and retained even in the absence of supply.

I claim:

1. A pocket calculator for the forecasting of temporal cycles, comprising: an electrical power supply, input means for inputting data corresponding to dates and calculation instructions to said calculator, electronic calculation means including means for receiving said data from said input means and means for carrying out temporal cycle forecasting calculations in response to the instruction data and for producing output signals corresponding to the results of said calculations, display means controlled by said output signals, an electromechanical memory for retaining variable data and including a plurality of electromechanical memory units, each electromechanical memory unit comprising a bistable electromechanical miniature relay having at least one control solenoid and means for maintaining the mechanical position of said relay even in the absence of power from said electrical power supply, so as to retain the variable data even if the electrical power supply is cut off, each said relay including a plurality of relay contacts for reading the position of the relay and hence the variable data stored therein, said electromechanical memory further comprising writing means selectively actuatable for transmitting a writing pulse to each said relay and reading circuit means selectively actuatable for reading the position of each relay at the respective relay contacts thereof, the actuation of said reading means and said writing means being controlled by said electronic calculation means, and wherein said electromechanical memory is coupled in circuit to be read only by the electronic calculation means and for having date information written thereinto by successive introduction of data by manual actuating of the input means and wherein said calculator further includes a write control key and a safety key, said electronic calculation means being responsive to said write control key and said safety key for actuating said writing means only when said write control key and said safety key are simultaneously actuated.

2. A pocket calculator according to claim 1 wherein said input means comprises a numerical keyboard.

3. A pocket calculator according to claim 1 and further including a time base and logical electronic circuit means for effecting time measurement, and wherein said electronic calculation means includes means for the measurement and display of time in response to said time base and logical electronic circuit means.

4. A pocket calculator according to claim 1 wherein said electronic calculation means includes a central processor unit, and further including a first memory means comprising a ROM for containing data corresponding to said instructions in a form usable by said central processor unit.

5. A pocket calculator according to claim 4 wherein said ROM is replaceable, whereby different instructions may be provided for said central processor unit.

6. A pocket calculator according to claim 5 wherein said ROM comprises an EPROM, whereby the instructions for said central processor unit may be altered.

7. A calculator according to claim 1 wherein said display means includes a plurality of electro-optical elements for indicating said results of said calculations.

8. A pocket calculator according to claim 1 wherein said display means includes a plurality of electroluminescent elements in different colors.

9. A pocket calculator according to claim 1 wherein said display means includes a numerical display for displaying at least the data input to said calculator by said input means.

10. A pocket calculator according to claim 9 wherein said input means comprises a plurality of keys and wherein said electronic calculation means includes register means controlled by said keys and wherein said display means is responsive to said register means for numerically displaying the contents thereof.

11. A pocket calculator according to claim 10 wherein said register means includes means for incrementing said numerical display at a first, relatively slow rate, and thereafter at a second, relatively rapid rate.

12. A pocket calculator according to claim 11 wherein said keys further include at least one register control key, and said register means includes means responsive to actuation of said register control key for alternatively incrementing or decrementing said numerical display.

13. A pocket calculator according to claim 1 wherein said display means comprises an alphanumeric display.

* * * * *